United States Patent [19]
Guy et al.

[11] Patent Number: 5,682,940
[45] Date of Patent: Nov. 4, 1997

[54] METHOD FOR FORMING CURVED, RECTANGULAR BODIED NEEDLE BLANKS FROM TUBULAR STOCK

[75] Inventors: Thomas D. Guy, Hobe Sound, Fla.; Terry C. Eisensmith, Guilford, Conn.; Donald A. Morin, Goffstown, N.H.

[73] Assignee: United States Surgical Corporation, Norwalk, Conn.

[21] Appl. No.: 590,226

[22] Filed: Jan. 23, 1996

[51] Int. Cl.[6] ............................................. B21G 1/00
[52] U.S. Cl. .................. 163/5; 29/417; 29/558; 83/54; 83/862; 83/875
[58] Field of Search .................. 163/1–5; 29/558, 29/414, 417; 83/875, 862, 54, 191, 684–686; 409/259, 268, 307, 304

[56] References Cited

U.S. PATENT DOCUMENTS

| | | |
|---|---|---|
| 1,735,759 | 11/1929 | Hofmann et al. . |
| 4,672,734 | 6/1987 | Kawada et al. . |
| 4,785,868 | 11/1988 | Koenig, Jr. . |

FOREIGN PATENT DOCUMENTS

| | | |
|---|---|---|
| 0650698 | 5/1995 | European Pat. Off. . |
| 2947806 | 11/1979 | Germany . |

*Primary Examiner*—Daniel C. Crane

[57] ABSTRACT

There is disclosed an apparatus for forming curved and rectangular bodied needle blanks from a length of needle stock which includes a generally cylindrical inner mandrel having a plurality of longitudinal channels formed in an outer surface thereof, the mandrel being dimensioned and configured for insertion within the length of needle stock. The apparatus also includes a plurality of broaches insertable into the longitudinal channels such that an edge of each broach projects radially outwardly of the mandrel to form a plurality of inner grooves on an inner surface of the length of needle stock. There is also provided structure for forming outer grooves in an outer surface of the length of needle stock to form a substantially grooved length of needle stock, cutters for cutting the grooved length of needle stock to form rings of curved rectangular bodied needle blanks interconnected by web portions and structure for dividing the rings at the web portions to form a plurality of curved rectangular bodied needle blanks. There is also disclosed a method of forming needle blanks from a length of needle stock having a longitudinal cavity therethrough and defining a longitudinal axis by forming at least two inner grooves in an inner surface of the length of needle stock and substantially parallel to the longitudinal axis, forming a number of outer grooves, equal to the number of inner grooves, in an outer surface of the length of needle stock and in substantial radial alignment with the at least two inner grooves to form a grooved length of needle stock and sectioning the grooved length of needle stock to form individual needle blanks.

9 Claims, 7 Drawing Sheets

Fig. 12

METHOD FOR FORMING CURVED, RECTANGULAR BODIED NEEDLE BLANKS FROM TUBULAR STOCK

BACKGROUND

1. Technical Field

The technical field relates generally to the formation of surgical needle blanks, and more particularly, to apparatus for forming needle blanks and methods for forming curved and rectangular bodied needle blanks from a ring, or length of needle stock formed to produce a ring.

2. Description of Related Art

The production of needles involves many processes and different types of machinery in order to prepare quality needles from raw stock. These varying processes and machinery become more critical in the preparation of surgical grade needles where the environment of intended use is in humans or animals. Some of the processes involved in the production of surgical grade needles include, inter alia, straightening wire stock from a reservoir, cutting needle blanks from wire stock, tapering or grinding points on one or both ends of the blank, and providing structure for receiving a suture thread at an end of the blank or at a location intermediate the ends. As used herein, the term "needle blank" refers to a piece of needle stock at various stages of completion but not fully formed into a surgical grade needle suitable for use during surgical procedures. Additionally, one skilled in the art will appreciate that flat surfaces may be formed on sides of the blank, typically by flat pressing portions of the needle blank to facilitate grasping by surgical instrumentation. Curving of the needle blank may also be performed where curved needles are desired. When providing curved and flat side or rectangular bodied needles for surgical procedures it is desirable for the needles to have a specified rectangular cross-section and a specified curvature, i.e., a predetermined radius of curvature. The desired cross-section and radius of curvature for the finished needle varies with specific applications.

When forming flat sided or rectangular bodied needle blanks, the needle blank material is compressed and deformed during the pressing operation thereby raising the potential for creating unwanted stresses in the needle blank. Further, when surgical grade needles are made of steel or similar resilient materials, the curving anvil or mandrel used must have a smaller radius than the desired radius of the final surgical needle. This configuration compensates for a "springback" or radial expansion effect after the curving operation to ensure that the desired radius of curvature is attained.

Certain types of surgical grade needles, such as, for example, double pointed and curved needles, or surgical incision members, typically require several processes to form the finished product. These processes may include curving and cutting needle stock to form needle blanks, altering or refining the tip configurations and curvature radius, punching or drilling the blank to form a suture hole and/or notching the blank to provide engaging structure for cooperative instrumentation.

Conventional needle processing is, in large part, a labor intensive operation requiring highly skilled labor. One disadvantage to conventional needle processing is that most needle processing operations, such as, for example, cutting the blanks from stock, tapering the stock to form points, flat and side pressing of the body portion of the blanks, curving the blanks, etc., must be performed on separate processing machines.

Thus it would be desirable to have an apparatus for forming a large number of curved and rectangular bodied needle blanks, suitable for further finishing and refining, in a very short time and with a minimal amount of machinery. It would further be desirable to have an apparatus and a method of forming curved needle blanks having a desired radius of curvature without having to compensate for springback or other alterations of curvature radius. It would be still further desirable to have an apparatus and a method of forming flat sided or rectangular bodied needle blanks without having to press or compress the needle blank material.

SUMMARY

The disclosed surgical instrumentation relates to apparatus for forming needle blanks from a ring of needle stock or, alternatively, a length of material manipulated to form such a ring. Broadly stated, the apparatus generally includes supporting structure for supporting the ring of needle stock and machining structure for imparting a plurality of needle blank shapes in the ring of needle stock. In one embodiment, the apparatus includes an inner mandrel having at least one broach receiving channel formed in an outer surface thereof and being dimensioned and configured to fit within the ring of needle stock. At least one broach is provided and is configured for slidable insertion within the broach receiving channel such that at least a portion of the broach projects beyond the outer surface of the mandrel. When positioned within the channel, the projecting portion of the broach forms grooves in an inner surface of the ring of needle stock surrounding the mandrel. The apparatus further includes structure for forming grooves on an outer surface of the ring of needle stock in substantial radial alignment with the grooves in the inner surface of the ring of needle stock, and cutters for cutting the grooved ring of needle stock to form individual needle blanks.

The inner mandrel is preferably configured and dimensioned to fit the shape defined by the inner circumferential surface of the ring of needle stock. The broach preferably has a leading cutting edge and at least one tapered side edge. The apparatus may further include driving structure to drive the broaches within the channels.

There is also disclosed a method of forming a needle blank from a ring of needle stock by mechanically imparting a plurality of needle blank shapes into the material of the ring of needle stock.

Preferably, this is accomplished by forming at least two inner grooves in an inner surface of the ring of needle stock and substantially parallel to a longitudinal axis thereof and forming a number of outer grooves, equal to the number of inner grooves, in an outer surface of the ring of needle stock and in substantial radial alignment with the at least two inner grooves to form a grooved ring of needle stock. Thereafter, the grooved ring of needle stock is sectioned to form individual needle blanks. The step of sectioning preferably includes cutting the grooved ring of needle stock substantially perpendicular to the longitudinal axis to form at least one ring of needle blanks interconnected by web portions defined by the inner and outer grooves, and severing the web portions to divide the ring into individual needle blanks.

In accordance with another embodiment, an apparatus for forming a ring of curved rectangular bodied needle blanks from a ring of needle stock is provided which includes a fixture to hold the ring of needle stock and a die having a pair of concentric cutting edges projecting therefrom. Each cutting edge of the die is dimensioned and configured to impart a series of alternating flat sided cuts to the ring of needle stock. Preferably, each of the concentric cutting edges alternates between arcuate segments of greater radius and arcuate segments of lesser radius such that the arcuate segments of greater radius of one of the pair of concentric cutting edges is in substantial radial alignment with the arcuate segments of lesser radius of the other concentric cutting edge.

BRIEF DESCRIPTION OF THE DRAWINGS

Various embodiments are described herein with reference to the drawings, wherein.

DESCRIPTION OF PREFERRED EMBODIMENTS

The preferred embodiments illustrated and discussed herein are directed to the ultimate formation of a surgical incision member for use in remote suturing in a body cavity. It is contemplated that the illustrated structure and methods can readily be used in the formation of any needle configuration including single pointed needles, needles of varying cross-sectional shapes, straight needles, etc.

Figure 1:
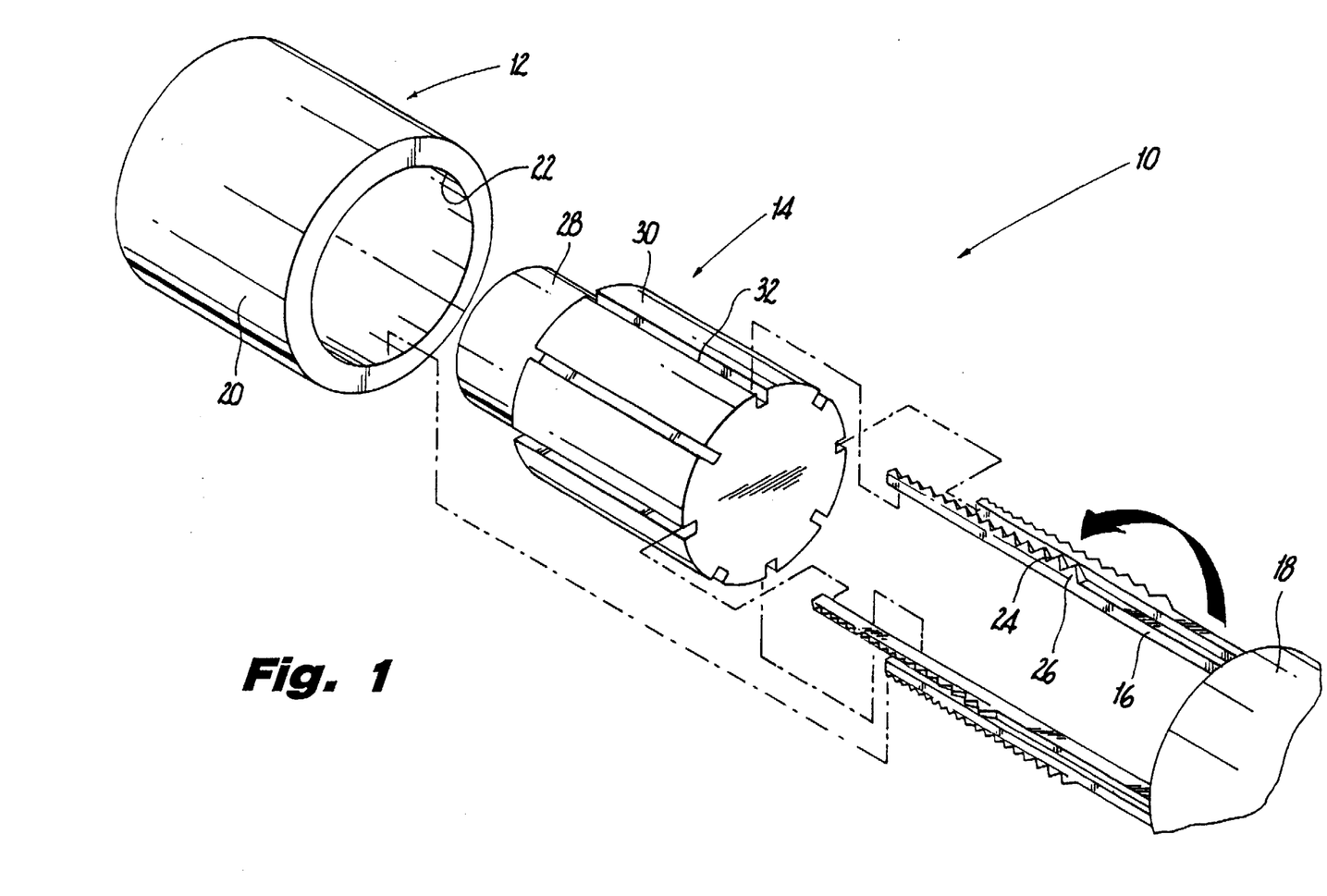
FIG. 1 is a perspective view of an apparatus for forming curved rectangular bodied needle blanks from a length of needle stock with parts separated.

Referring now to FIG. 1, an apparatus 10 is illustrated which is particularly suited to form a series of longitudinal cuts in a tube or ring of needle stock such as, for example, length of tubular needle stock 12, in order to partially form a number of curved and pre-pointed needle blanks therein. Apparatus 10 generally includes support structure for supporting a ring of needle stock 12. In this embodiment the support structure includes an inner mandrel 14 which is insertable within tubular needle stock 12. Means for imparting a plurality of needle blank shapes is also provided. In this embodiment, the means for imparting a plurality of needle blank shapes includes at least one cutting die or broach 16 which, when forced between inner mandrel 14 and tubular needle stock 12, imparts a longitudinal groove in tubular needle stock 12. Apparatus 10 additionally includes a driver 18 which is configured for driving broach 16 between inner mandrel 14 and length tubular needle stock 12.

Figure 4:
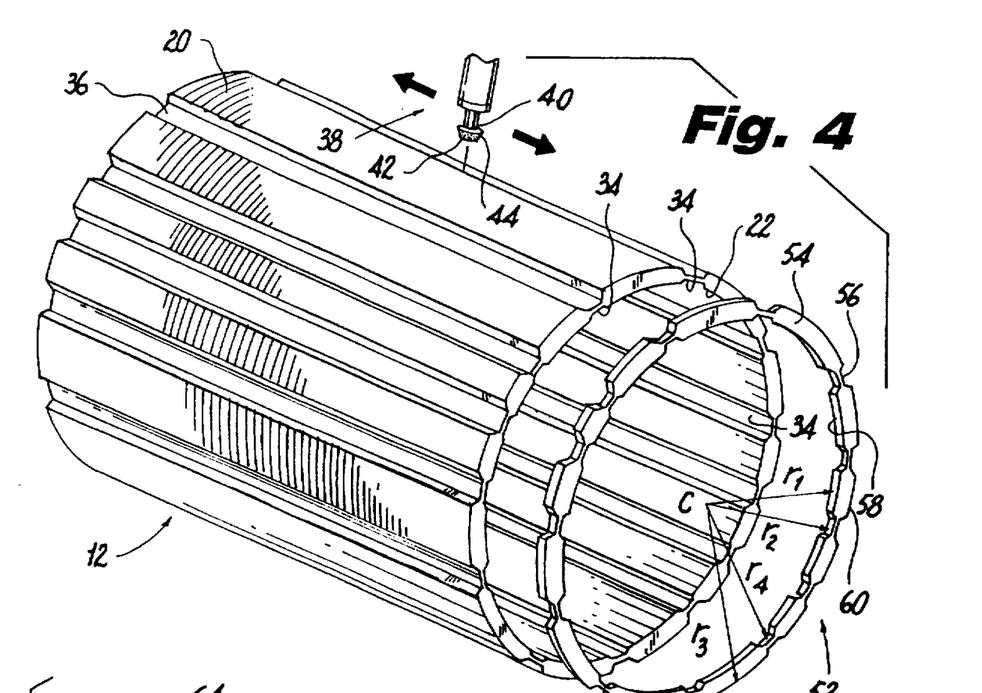
FIG. 4 is a perspective view of the length of needle stock, grooved on inner and outer surfaces thereof, and sliced to form a ring of curved rectangular bodied needle blanks.

Preferably, tubular needle stock 12 consists of tubular shaped bicompatable material of the type suitable for forming surgical grade needles such as, for example, stainless steel, etc. Preferably, tubular needle stock 12 has a wall thickness selected generally to conform to the thickness of a finished surgical needle. In order to form tubular needle stock 12 into surgical needle blanks it is desirable to impart a series of longitudinal grooves along both an outer surface 20 and an inner surface 22 of tubular needle stock 12. The longitudinal grooves along inner surface 22 of tubular needle stock 12 are formed using broaches 16, preferably formed with a leading cutting edge 24 and side cutting edges 26. When these cutting edges 24, 26 are forced between inner mandrel 14 and inner surface 22 of tubular needle stock 12, a longitudinal three sided groove 34 is formed within inner surface 22 (FIG. 4).

Inner mandrel 14 is preferably dimensioned and configured to fit closely within tubular needle stock 12. Inner mandrel 14 is provided with a mounting potion 28 for attachment to an external holding fixture 17, (see FIG. 2) and a broach retaining potion 30 configured to guide broaches 16 between inner mandrel 14 and inner surface 22 of tubular needle stock 12. Mounting portion 28 is configured to be held by the external holding fixture such that inner mandrel 14 does not move as broaches 16 are driven therealong. Preferably broach retaining potion 30 includes plurality of circumferentially spaced and longitudinally extending channels 32 which are adapted to receive broaches 16. When broaches 16 are inserted within channels 32, cutting edges 24 and 26 project from an outer surface of die retaining potion 30 to engage inner surface 22 of tubular needle stock 12. In this manner, as broaches 16 are moved by driver 18 within channels 32, cutting edges 24 and 26 projecting from mandrel 14 cut or score longitudinal grooves within inner surface 22 of tubular needle stock 12.

Figure 2:
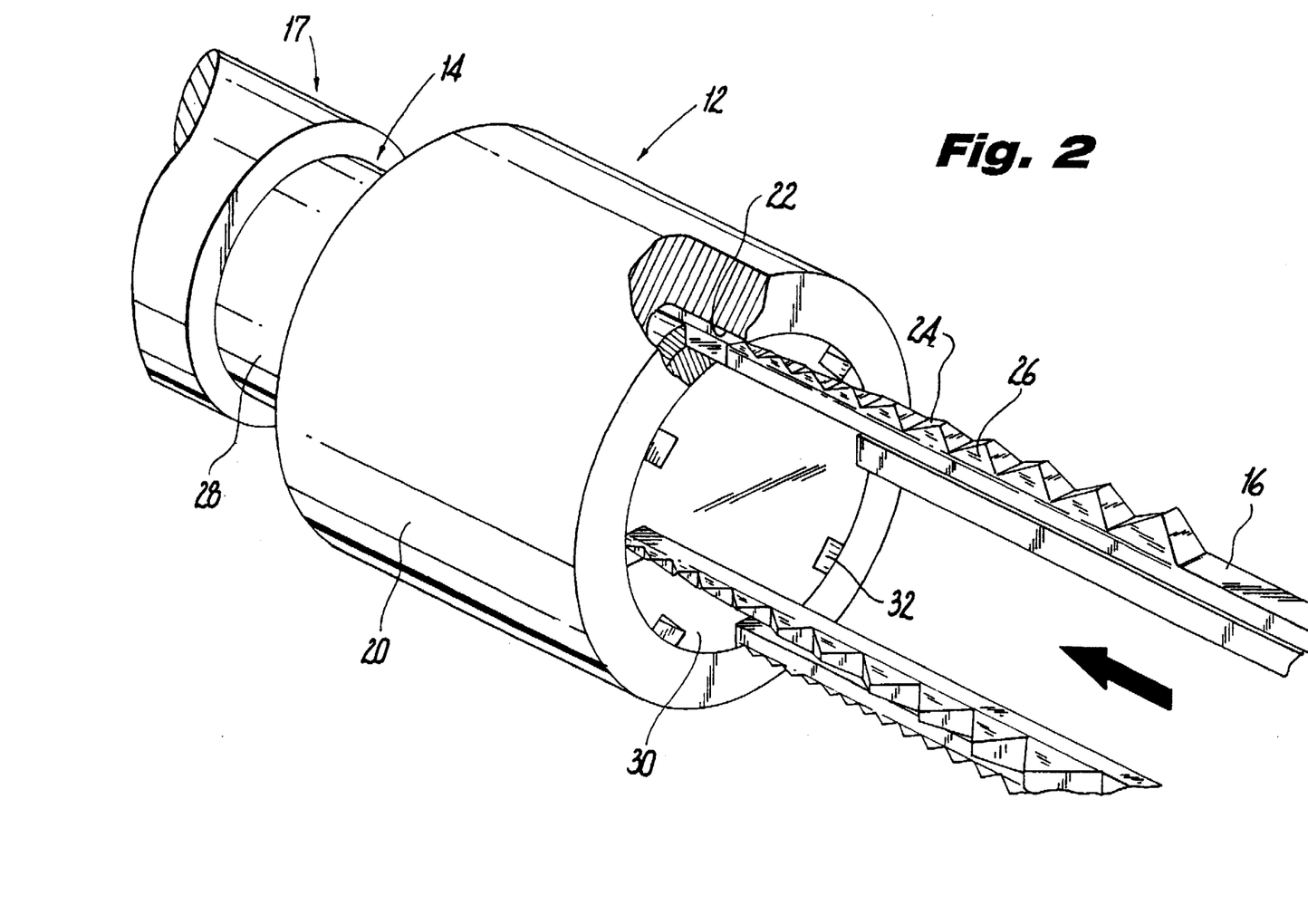
FIG. 2 is an assembled perspective view, partially in section, of the apparatus of FIG. 1.
Figures 3, 3A, 3B:
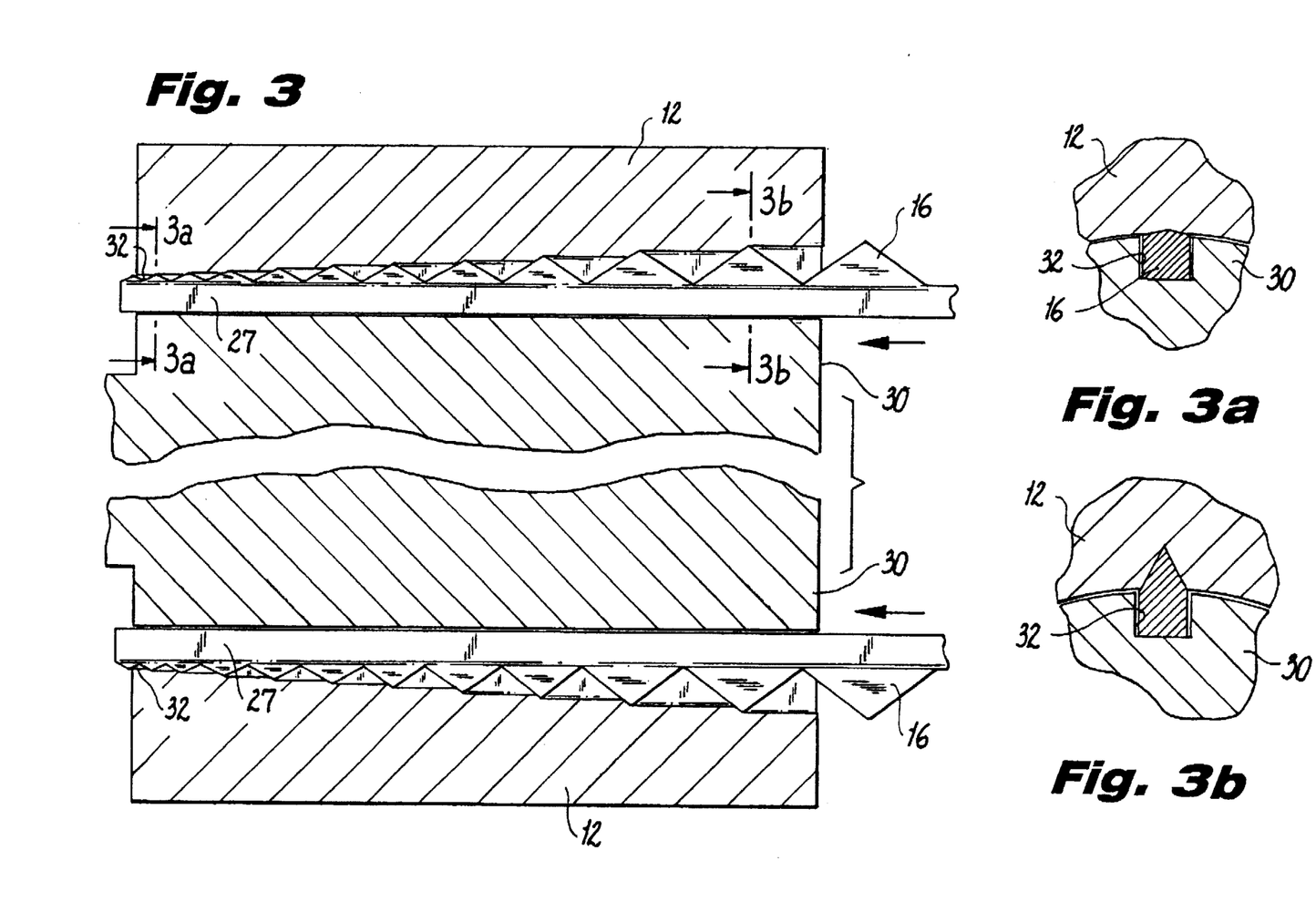
FIG. 3 is a partial cross-sectional view of the apparatus of FIG. 1 depicting a broach being forced between an inner mandrel and the length of needle stock.
FIG. 3a is cross-sectional view of a broach taken along line 3a—3a of FIG. 3.
FIG. 3b is a cross-sectional view taken along line 3b—3b of FIG. 3.

Referring now to FIGS. 2 and 3, in operation, inner mandrel 14 is initially positioned coaxially within tubular needle stock 12 and mounting portion 28 is mounted within a holding fixture 17. Broaches 16, which are mounted to driver 18, are inserted within channels 32 and forced longitudinally within channels 32 by driver 18 in order to score or cut grooves into inner surface 22 of tubular needle stock 12. Referring specifically to FIGS. 3, 3a and 3b, as broaches 16 are driven within channels 32, base portions 27 of broaches 16 ride within channels 32 while leading cutting and side edges 24 and 26, respectively, engage inner surface 22 of tubular needle stock 12 to progressively cut three sided grooves 34 within inner surface 22.

During broaching of inner surface 22 of tubular needle stock 12, it is preferable to securely hold tubular needle stock 12 against relative movement with respect to inner mandrel 14. Various non-destructive or non-marring methods, such as, for example, padded clamping etc. may be used to hold tubular needle stock 12 stationary with respect to inner mandrel 14 during the broaching operation.

Referring now to FIG. 4, after broaching, tubular needle stock 12 has a plurality of circumferentially spaced and longitudinally extending grooves 34 formed in inner surface 22. In order to form a plurality of interconnected needle blanks from tubular needle stock 12, means for forming grooves on an outer surface of the needle stock material are provided, in this embodiment, a grinder 38 is provided as the means for forming grooves on the outer surface. It is preferable to form an equal number of corresponding and longitudinally extending external grooves 36 in outer surface 20 of tubular needle stock 12 corresponding to the grooves 34 formed in the inner surface. Grinder 38 includes a grinding wheel 40 which is movable toward and away from tubular needle stock 12 and, more importantly, moveable longitudinally with respect to tubular needle stock 12 in order to impart grooves 36 corresponding to grooves 34. Although shown herewith a movable grinder 38, one skilled in the art will readily appreciate that a fixed grinder could be used and the needle stock material moved relative thereto.

Grinding wheel 40 can have any desired configuration depending upon the shape of the groove to be formed. Preferably, grinding wheel 40 includes a flush bottom cutting surface 42 and an angled side cutting surface 44 such that when grinder wheel is engaged and moved longitudinally along outer surface 20 it imparts a three sided groove 36 substantially similar to inner three sided grooves 34. Preferably, grooves 36 are formed in outer surface 36 in substantial radial alignment with inner grooves 34 formed in inner surface 22, that is, along the same radial lines, to define a series of needle blank segments and connected by web portions as more fully described hereinbelow.

Figure 4A:
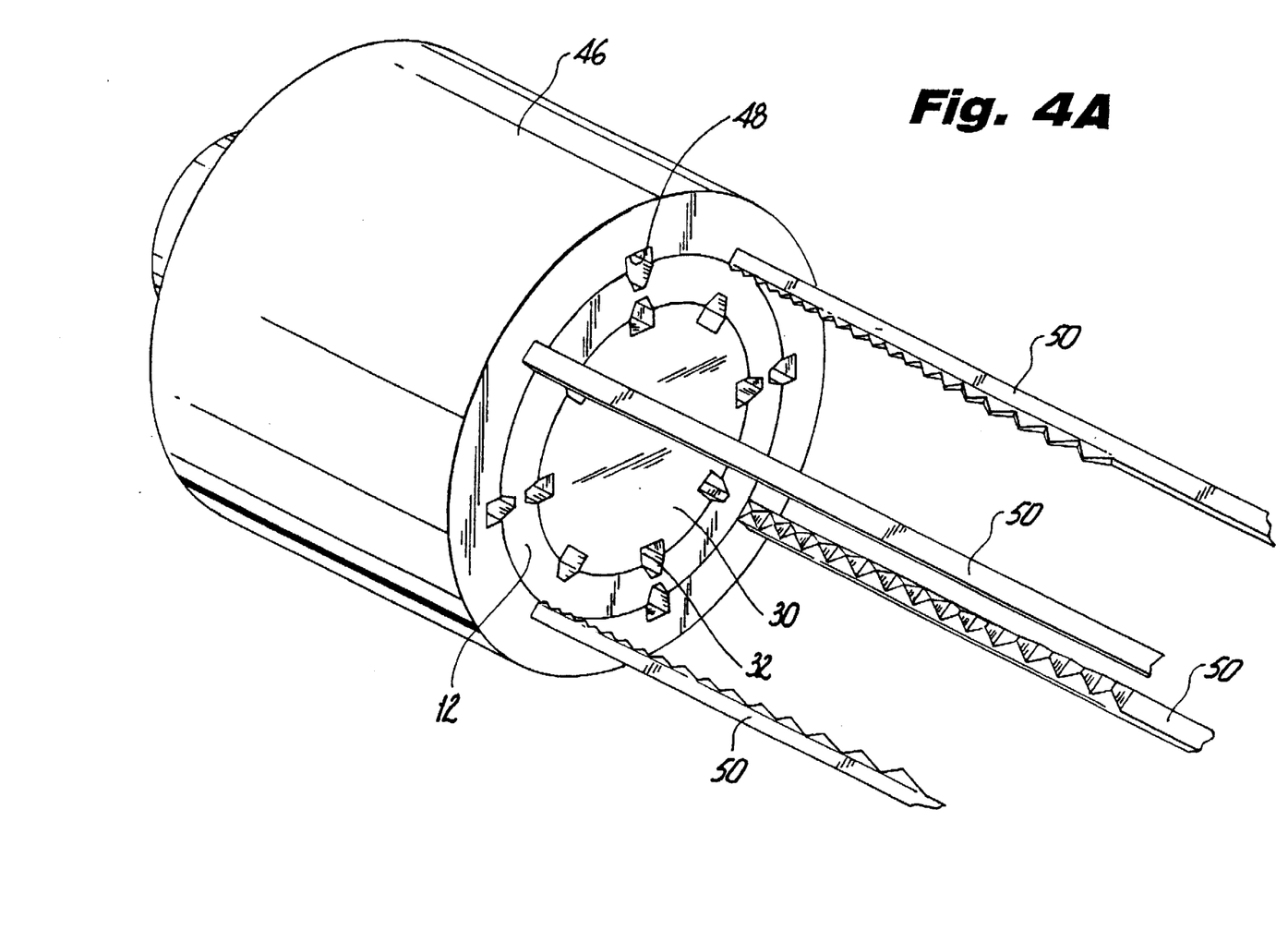
FIG. 4A is a perspective view of the length of needle stock illustrating an alternate method of forming grooves in an outer surface thereof.

Alternatively, it may be preferable to broach or cut grooves 36 into outer surface 20 in a manner substantially similar to the broaching of inner grooves 34. Referring to FIG. 4A, an outer member 46 is provided having a longitudinal channel 48 therein. Outer member 46 is configured to conform to the shape of the needle stock material around which it is positioned. In this embodiment, outer member 46 is formed as a cylinder into which tubular needle stock 12 is inserted. A broach 50, similar to broach 16, is longitudinally inserted within channel 38 and engages surface 20 of tubular needle stock 12 separately from, or optionally simultaneously with, the broaching of inner surface 22. Other apparatus or methods of forming grooves 36 in outer surface 20 are also contemplated and include providing structure for stamping die 50 into outer surface 20 in order to stamp grooves 36 into outer surface 20, as well as chemical or electromechanical etching, etc.

Referring back to FIG. 4, once grooves 34 and 36 have been formed within inner and outer surfaces 22 and 20 in tubular needle stock 12, respectively, grooved tubular needle stock 12 may be sectioned to form individual needle blanks. Tubular needle stock 12 is initially sliced perpendicular to its longitudinal axis to form rings 52, each containing a plurality of needle blanks 54 interconnected by web portions 56. Various methods may be used to slice or cut grooved tubular needle stock 12 into rings 52, such as, for example, by cutting with a saw type blade or with a laser cutter. Additionally stamping or grinding operations utilizing flat cutting action may be performed perpendicular to the longitudinal axis of grooved tubular needle stock 12 to form rings 52. Rings 52 are formed with a thickness corresponding to the desired needle thickness. Preferably, rings 52 are on the order of approximately 0.03 to 0.05 inches thick and, more preferably, approximately 0.034 inches thick. As used herein, the above described methods are means for cutting grooved tubular needle stock 12 substantially perpendicular to its longitudinal axis.

Rings 52 also may be formed by various methods or dies which impart a round rather than rectangular configuration to the ring 52 of needle blanks to ultimately form curved round-bodied needles rather than curved rectangular bodied needles.

Ring 52 has an inner circumferential surface 58 and an outer circumferential surface 60 which, due to inner and outer grooves 34 and 36, respectively, each have segments of alternating radii. For example, ring 52 has an inner radius r1 along that portion of inner circumferential surface 58 which was not broached and corresponds to inner surface 22. Inner circumferential surface 58 has a second radius r2 at web portions 56 which corresponds to broached channels 34. Similarly, outer circumferential surface 60 has an outer radius r3 which corresponds to unbroached outer surface 20 and an outer radius r4 which corresponds to longitudinally broached channels 36 in outer surface 20. Thus, the inner and outer circumferential surfaces, 58 and 60, respectively, of ring 52 alternate between various segments of greater and lesser radius to define a plurality of needle blank segments 54 interconnected by web potions 56. Depending on the spacings between adjacent grooves 34 or 36, needle blanks 54 may have equal or varying arcuate lengths. At this point, ring 52 may be taken to various other forming stations to impart various other characteristics to blanks 54, such as, for example, hole drilling, notching, polishing, stamping to form round-bodied needle blanks, etc.

Figure 5:
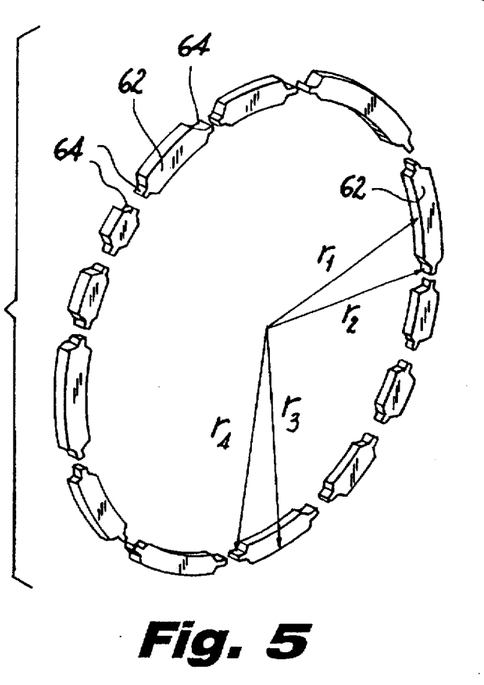
FIG. 5 is a perspective view of the grooved ring of needle stock sectioned to form curved, rectangular bodied needle blanks.

Referring now to FIG. 5, once ring 52 has been formed from grooved tubular needle stock 12, ring 52 may be divided at web potions 56 to form a plurality of individual needle blanks 62. As noted above, needle blanks 62 may have various arcuate lengths according to the distances between adjacent grooves 34, 36 formed in tubular needle stock 12 and preferably have a length of approximately 0.4 inches.

Figure 6:
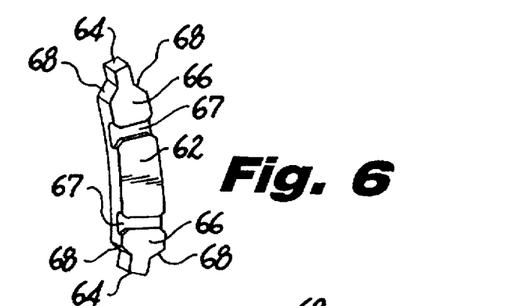
FIG. 6 is a perspective view of a curved, rectangular bodied needle blank formed by the apparatus of FIG. 1.

An individual needle blank 62 for ultimate processing into a surgical incision member is illustrated in FIG. 6 and generally includes cut web potions 64 formed on end potions 66 which, in conjunction with angled side potions 68, form an initial taper or pre-point at either end portion 66 of needle blank 62.

Figure 6A:
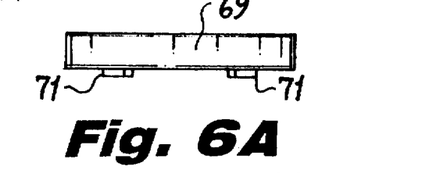
FIG. 6A is a side elevational view of a die for forming apparatus engagement notches in the needle blank of FIG. 6.
Figure 6B:
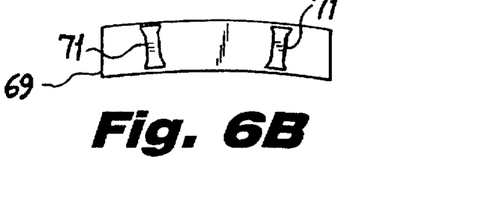
FIG. 6B is an end view of the die face of FIG. 6A.

Needle blank 62 may thereafter be taken to various other apparatus and processing stations for subsequent final tapering or pointing, imparting notches adjacent either end and hole drilling to form a surgical incision member, and, where round body needles are desired, may be pressed within various apparatus to form curved round bodied needles. Ends 66 may be finished on various taper grinding and pointing machinery. Referring to FIGS. 6, 6a and 6b, for example, notches 67 may be formed in needle blank 62 by stamping or coining with a die 69 (FIGS. 6A and 6B) having a pair of projecting notching surface 71.

Figure 7:
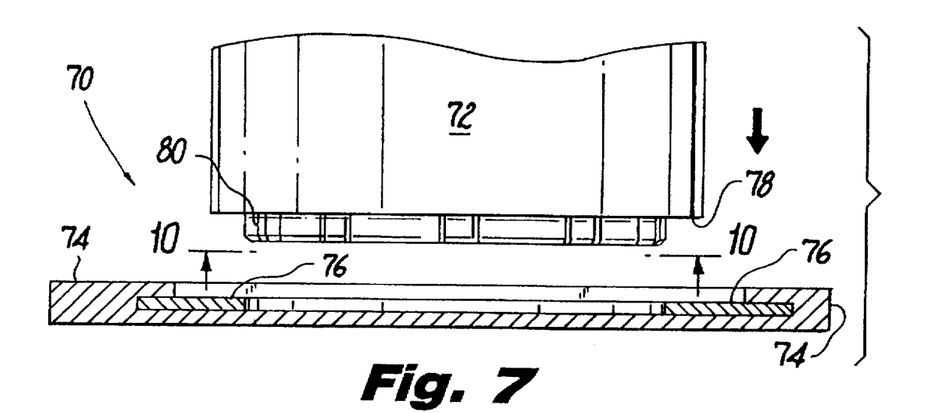
FIG. 7 is a side elevational view of an alternate embodiment of an apparatus for forming a ring of curved, rectangular bodied needle blanks.

Referring now to FIG. 7 there is disclosed an alternate apparatus for forming a ring of curved and double pre-pointed rectangular-bodied needle blanks. Apparatus 70 includes means for imparting a plurality of needle blank shapes in a ring of needle stock material. In this embodiment, cylindrical die 72 serves to impart a plurality of needle blank shapes into ring of needle stock 76. Supporting means for supporting the ring of needle stock 76 includes fixture 74. Ring of needle stock 76 is preferably formed of a biocompatible material similar to tubular needle stock 12.

Figure 8:
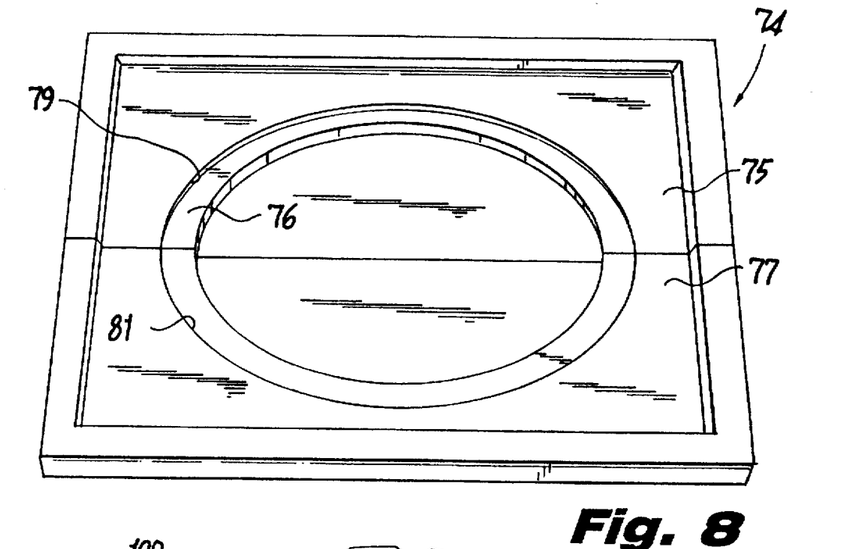
FIG. 8 is a perspective view of holding fixture holding a ring of needle stock.
Figure 9:
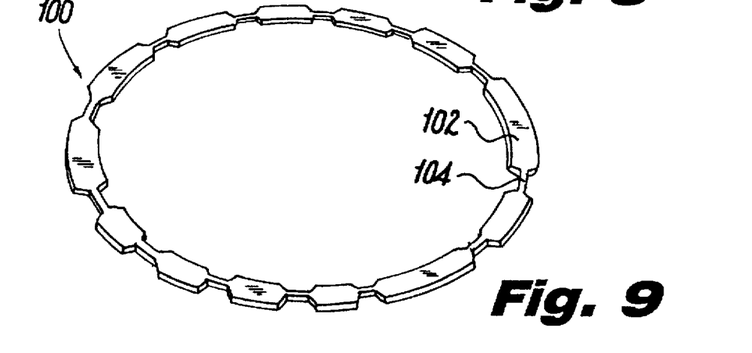
FIG. 9 is an perspective view of a needle blank ring cut from flat needle stock.
Figure 10:
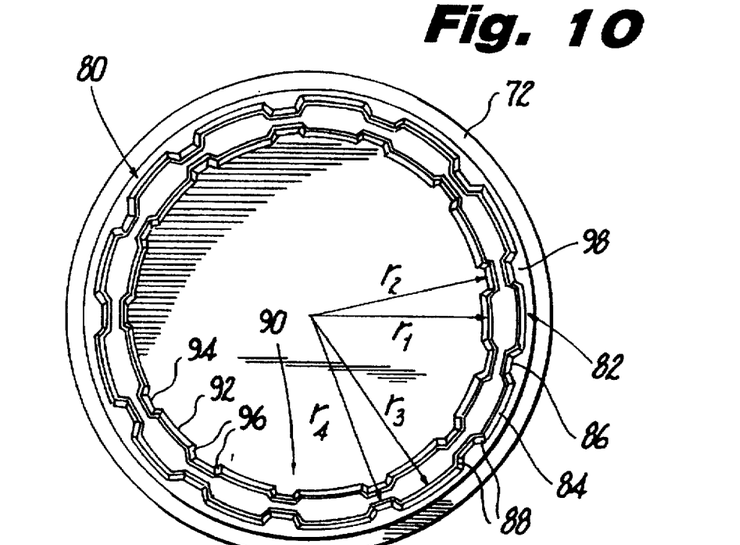
FIG. 10 is an end view taken along the line 10—10 of FIG. 7 showing the cutting die face of the apparatus of FIG. 7.

Referring to FIGS. 7, 9 and 10, die 72 has a die face 78 which includes a pair of concentric cutting edges 80 projecting therefrom. Cutting edges 80 generally include an outer cutting ring 82 which is used to impart a series of alternating circumferential segments within ring of needle stock 76 having greater and lesser radii r3 and r4, respectively, similar to that described hereinabove with respect to ring 52. Outer cutting ring 82 has outer circumferential cutting edges 84 having a radius r3 and outer web cutting edges 86 having a radius r4. Outer circumferential cutting edges 84 and outer web cutting edges 86 are interconnected by angled cutting edges 88. Similarly, inner cutting ring 90 has inner circumferential cutting edges 92 having an inner radius r1 and inner web cutting edges 94 having radius r2. Inner circumferential cutting and inner web cutting edges, 92 and 94, respectively, are interconnected by angled cutting edges 96. Outer circumferential cutting edge 84 of outer cutting ring 92 functions with inner circumferential cutting edge 92 of inner cutting ring 90 to cut the needle blank segment from ring of needle stock 76. Similarly, outer web cutting edge 86 functions with inner web cutting edge 94 to cut the web portions of a ring of needle blanks from ring of needle stock 76. Angled cutting edges 96 serve, along with angled cutting edges 88, to pre-point needle blanks contained within a ring of cut needle material. It will be appreciated that cutting edges 80 may be contained in a separate die body 98 which is removably attached to die 72 in order to vary the radii of the arcuate segments, as well as the lengths of the individual needle blanks, cut within the ring and the angles of the pre-points. Referring to FIG. 8, fixture 74 preferable includes a pair of separable halves 75 and 77 each having a semi-circular inner holding portion 79 and 81, respectively. Fixture halves 75 and 77 are connectable to firmly hold ring of needle stock 76 between semi-circular inner holding portions 79 and 81 during the stamping operation.

In operation, die 72 is forced down against ring of needle stock 76 causing cutting edges 80 to cut ring 100 out of ring of needle stock 76. Ring 100 includes a plurality of needle blanks 102 interconnected by web portions 104. Once ring 100 has been cut fixture halves 75 and 77 may be separated to release ring 100 and ring 100 may be segmented into various individual needle segments or blanks similar to needle blanks 62 described hereinabove.

Referring now to FIG. 9, a needle blank ring 100 is shown and is similar to needle blank ring 52 described hereinabove. Needle blank ring 100 can subsequently be taken to various processing stations for segmenting and various other operations, such as, hole drilling, notching, taper point finishing, etc.

Figure 11:
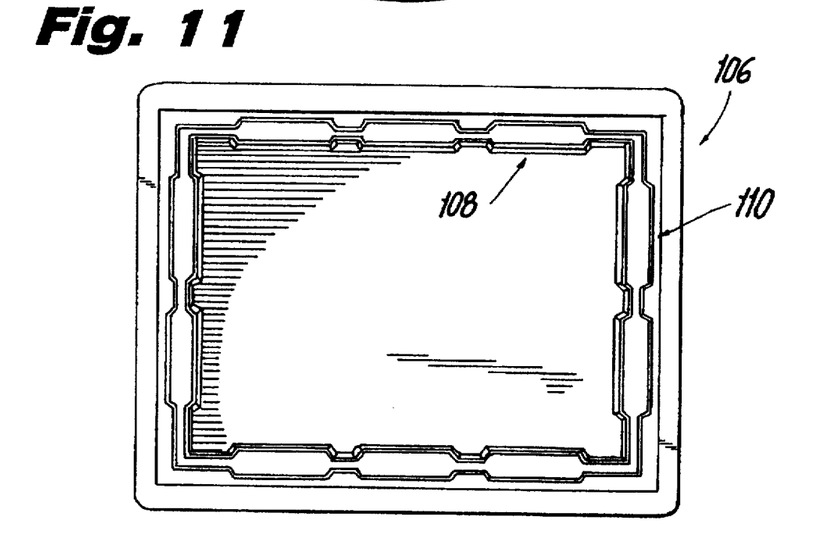
FIG. 11 is an end view of an alternate cutting die face for forming straight, rectangular bodied needle blanks.
Figure 12:
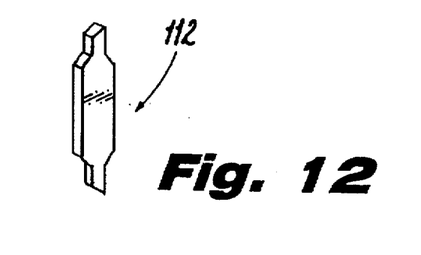
FIG. 12 is a perspective view of a straight, rectangular bodied needle blank.

Referring now to FIG. 11, there is disclosed an alternate die 106 for forming a plurality of straight and rectangular bodied needle blanks from a rectangular ring or flat sheet of needle stock. Die 106 has a pair of inner and outer cutting edges 108 and 110 which, like cutting edges 82 and 90 described hereinabove, alternate between interconnected segments in order to cut a plurality of straight needle blanks interconnected by web portions from the rectangular ring of needle stock. A straight, pre-pointed and rectangular bodied needle blank 112 cut by die 106 is best illustrated in FIG. 11.

It will be understood that various modifications may be made to the embodiments disclosed herein. For example, the inner mandrel may have a variety of shapes, such as, for example, elliptical to form needle blanks of varying radius, or of a rectangular cross-section such that when the inner mandrel is disposed within a rectangular tube of needle stock material the rectangular tube of needle stock material may be broached, ground or stamped to form a series of interconnected straight rectangular bodied needle blanks which may be subsequentially divided to form a plurality of individual straight and rectangular needle blanks. Therefore, the above description should not be construed as limiting, but merely as exemplifications as preferred embodiments. Those skilled in the art will envision other modifications within the scope and spirit of the claims appended hereto.

What is claimed is:

1. A method for forming needle blanks from a ring of needle stock comprising the steps of: providing a ring of needle stock; supporting the ring of needle stock; and imparting a plurality of needle stock shapes in the supported ring of needle stock to form the needle blanks.

2. A method of forming a ring of interconnected curved needle blanks from needle stock comprising the steps of:
   a) forming an inner circumferential surface within a needle stock material, the inner circumferential surface having arcuate segments that alternate between segments of a greater radius and segments of a lesser radius; and
   b) forming an outer circumferential surface in the needle stock, the outer circumferential surface having arcuate segments that alternate between segments of greater radius and segments of lesser radius, said formed inner and outer circumferential surfaces defining a ring of interconnected curved needle blanks.

3. The method according to claim 2, wherein the outer circumferential surface is formed concentric with the inner circumferential surface.

4. The method of claim 2, wherein the arcuate segments of greater radius of the outer circumferential surface are formed in substantial radial alignment with the arcuate segments of lesser radius of the inner circumferential surface.

5. A method of forming needle blanks from a ring of needle stock having a longitudinal cavity therethrough comprising:
   a) providing a ring of needle stock defining a coaxial longitudinal axis having a length;
   b) forming at least two inner grooves in an inner surface of the ring of needle stock and substantially parallel to the longitudinal axis;
   c) forming a corresponding number of outer grooves, equal to the number of inner grooves, in an outer surface of the ring of needle stock and in substantial alignment with the at least two inner grooves to form a grooved ring of needle stock; and
   d) sectioning the grooved ring of needle stock to form individual needle blanks.

6. The method according to claim 5 wherein the step of sectioning includes:
   a) cutting the grooved ring of needle stock substantially perpendicular to the longitudinal axis to form at least one ring of needle blanks interconnected by web portions defined by the inner and outer grooves; and
   b) severing the web portions to divide the at least one ring into individual needle blanks.

7. The method according to claim 5 wherein the step of forming at least two inner grooves includes forcing a broach against the inner surface of the ring of needle stock to form the at least two inner grooves therein.

8. The method according to claim 7 wherein the step of forcing a broach against an inner surface of the length of needle stock includes:

a) inserting a mandrel within the longitudinal cavity of the length of needle stock; and b) forcing the broach between the mandrel and the inner surface of the length of needle stock to form a longitudinal groove in the inner surface of the length of needle stock.

9. The method according to claim 5 further comprising the step of notching an edge of the individual needle blanks adjacent an end of the individual needle blanks.

* * * * *